(12) United States Patent
Song et al.

(10) Patent No.: US 8,801,803 B2
(45) Date of Patent: Aug. 12, 2014

(54) CONNECTION STRUCTURE OF ARTIFICIAL LIMB AND SOCKET, USING MAGNETIC LOCKING DEVICE

(75) Inventors: Jum-Sik Song, Incheon (KR); Suk-Min Lee, Seoul (KR); Guk-Chan Cha, Incheon (KR); Sung-Hee Jung, Gyeonggi-do (KR); Ji-Yeon Lee, Gyeonggi-do (KR); Mu-Sung Mun, Seoul (KR); Soon-Jong Kim, Incheon (KR)

(73) Assignee: Korea Workers' Compensation & Welfare Service, Seoul (KR)

( * ) Notice: Subject to any disclaimer, the term of this patent is extended or adjusted under 35 U.S.C. 154(b) by 197 days.

(21) Appl. No.: 13/390,656

(22) PCT Filed: Nov. 30, 2009

(86) PCT No.: PCT/KR2009/007071
§ 371 (c)(1),
(2), (4) Date: Feb. 15, 2012

(87) PCT Pub. No.: WO2011/065608
PCT Pub. Date: Jun. 3, 2011

(65) Prior Publication Data
US 2012/0143350 A1    Jun. 7, 2012

(51) Int. Cl.
*A61F 2/60* (2006.01)
*A61F 2/78* (2006.01)
*A01H 9/00* (2006.01)

(52) U.S. Cl.
USPC .............................................. 623/32; 335/205

(58) Field of Classification Search
USPC ....................................... 623/33, 32; 335/205
See application file for complete search history.

(56) References Cited

U.S. PATENT DOCUMENTS

| | | | |
|---|---|---|---|
| 6,273,918 B1 * | 8/2001 | Yuhasz et al. | 623/33 |
| 6,517,585 B1 | 2/2003 | Zahedi et al. | |
| RE39,961 E | 12/2007 | Petrofsky et al. | |
| 2005/0101693 A1 * | 5/2005 | Arbogast et al. | 523/122 |
| 2005/0149202 A1 * | 7/2005 | Schaffer et al. | 623/36 |
| 2006/0293762 A1 | 12/2006 | Schulman et al. | |
| 2007/0156252 A1 | 7/2007 | Jonsson et al. | |

FOREIGN PATENT DOCUMENTS

| | | |
|---|---|---|
| JP | 2001-514924 A | 9/2001 |
| KR | 10-2006-0109786 A | 10/2006 |
| KR | 2006-0105026 A | 10/2006 |
| KR | 10-2006-0112458 A | 11/2006 |
| WO | WO 99/08621 A2 | 2/1999 |
| WO | WO 2005/051248 A1 | 6/2005 |

OTHER PUBLICATIONS

International Search Report for Application No. PCT/KR2009/007071 dated Aug. 25, 2010.

* cited by examiner

*Primary Examiner* — David Isabella
*Assistant Examiner* — Jacqueline Woznicki
(74) *Attorney, Agent, or Firm* — Alston & Bird LLP

(57) ABSTRACT

The present invention relates to a structure for connecting an artificial limb and a socket, in which a magnetic locking device is mounted on one end of the artificial limb. The magnetic locking device includes an electro-permanent magnet comprising a permanent magnet and an electromagnet, and one end of the socket is provided with an attachment member capable of being attached to or detached from the magnetic locking device using magnetic force.

6 Claims, 7 Drawing Sheets

CONNECTION STRUCTURE OF ARTIFICIAL LIMB AND SOCKET, USING MAGNETIC LOCKING DEVICE

CROSS REFERENCE TO RELATED APPLICATIONS

This application is a national stage application filed under 35 U.S.C. 371 of International Application No. PCT/KR2009/007071, filed Nov. 30, 2009, which is incorporated herein in its entirety.

TECHNICAL FIELD

The present invention relates, in general, to a structure for connecting an artificial limb and a socket liner that receives a stump, and more particularly, to a structure for connecting an artificial limb and a socket liner, in which the artificial limb and the socket liner are easily attached to and detached from each other using a magnetic locking device having a electro-permanent magnet.

BACKGROUND ART

Artificial limbs are man-made devices that are fabricated such that their appearance or function can replace that of a missing part of an arm or a leg. Some types of artificial limbs have the same shape and function as those of a missing joint. Although there are several categories of artificial limbs depending on the purpose and parts to be used, they are generally divided into an upper artificial limb that is commonly referred to as an artificial arm and a lower artificial limb that is commonly referred to as an artificial leg.

In order to use an artificial limb, first, a socket liner is worn on a stump, and the artificial limb is then connected to the socket liner. Most devices for connecting the artificial limb to the socket liner in the related art use a pin lock, which fixes the artificial limb and the socket liner using a pin. As shown in FIG. 2, the pin lock is a type of locking mechanism in which the socket liner is connected to the artificial limb by fixing a metal pin P to the distal connecting end of the socket liner. In the case of the pin lock, the area where the stump and the artificial limb are connected is only the cross-sectional area of the pin P. Consequently, it is difficult to balance the weight of the body in the standing position, and a gap in a fastening portion causes noises when walking.

FIG. 2 is a configuration view showing the fastening of a pin locking device of the related art (left) and the fastening of a magnetic locking device for an artificial limb according to the present invention (right). As shown in the figure, the pin lock has a long connecting portion where the stump and the artificial limb are connected. This structure, however, is difficult to use if the stump is long. In contrast, the magnetic lock is configured to be thin, and thus can be advantageously used even if the stump is long.

DISCLOSURE

Technical Problem

Accordingly, the present invention has been made keeping in mind the above problems occurring in the related art, and is intended to develop a magnetic locking device based on a electro-permanent magnet, in which a permanent magnet and an electromagnet are combined, and to develop a socket liner that interacts with the magnetic locking device, in order to provide a structure for connecting an artificial limb and a socket liner, in which the artificial limb and the socket liner can be easily attached to and detached from each other using the magnetic locking device having the electro-permanent magnet.

Technical Solution

In an aspect, the present invention provides a structure for connecting an artificial limb and a socket, including: a magnetic locking device disposed on a distal end of the artificial limb. The magnetic locking device has an electro-permanent magnet including a permanent magnet and an electromagnet. The structure also includes an attachment member disposed on a distal end of the socket. The attachment member is attachable to and detachable from the magnetic locking device using a magnetic force.

In the present invention, the magnetic locking device may include: a core for transmitting a magnetic field generated by the permanent magnet toward the attachment member; the permanent magnet disposed inside the core to generate the magnetic field; and an electric coil disposed on the core, wherein the electric coil generates a magnetic field so that the attachment member becomes easily attachable to and detachable from the magnetic locking device.

In the present invention, a magnetic flux generated by the permanent magnet may flow through the core and the attachment member to generate a force of attraction between the permanent magnet and the attachment member, and a current may be induced through the electric coil to generate a magnetic field in a direction inverse to that of the magnetic field of the permanent magnet in order to block a magnetic force generated by the permanent magnet, so that the magnetic flux generated by the permanent magnet may circulate inside the core, thereby canceling the force of attraction between the permanent magnet and the attachment member, whereby the permanent magnet and the attachment member may become easily detachable from each other.

In the present invention, the structure may also include: a battery for powering the magnetic locking device; a current regulator for regulating a current supplied to the magnetic locking device; and a power switch for switching on/off supply of power to the magnetic locking device.

In the present invention, power from the battery may be used only when detaching the artificial limb and the socket from each other.

In the present invention, a socket liner made of silicone may be disposed inside the socket, and a one-directional span raw material may be attached to a surface of the socket liner. The one-directional span raw material may be expandable and contractible only in a width direction but not in a longitudinal direction.

In the present invention, the socket liner may have a dual structure including an inner member, which is made of silicone having a Shore A hardness ranging from 5 to 20, and an outer member, which is made of silicone having a Shore A hardness ranging from 30 to 60.

MAJOR REFERENCE NUMERALS OF THE DRAWINGS

Figure 1:
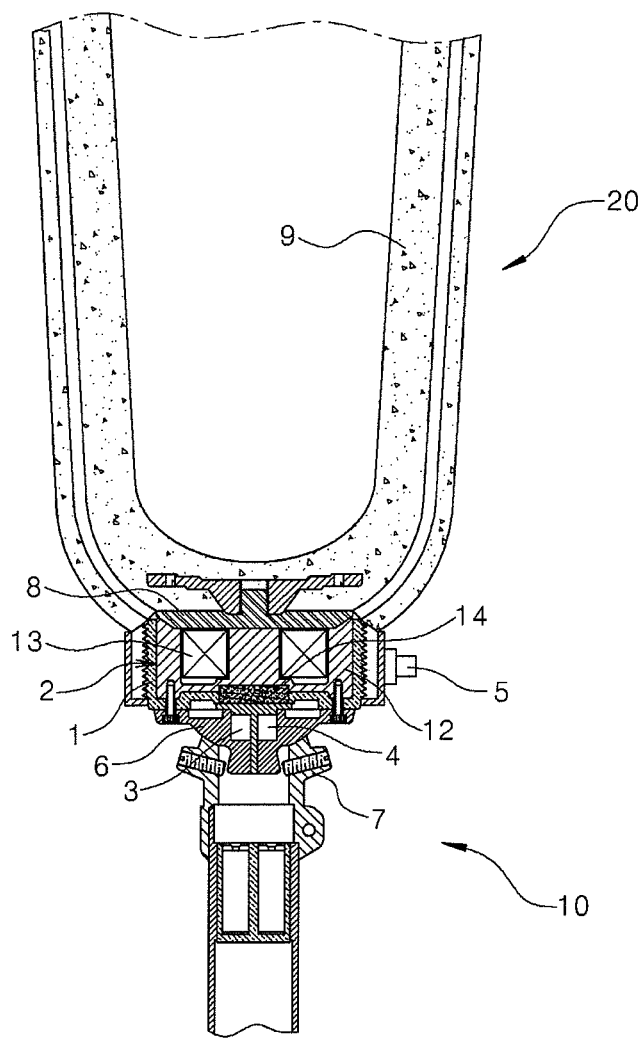
FIG. 1 is a cross-sectional view showing a structure for connecting an artificial limb and a socket using a magnetic locking device according to the present invention.
Figure 2:
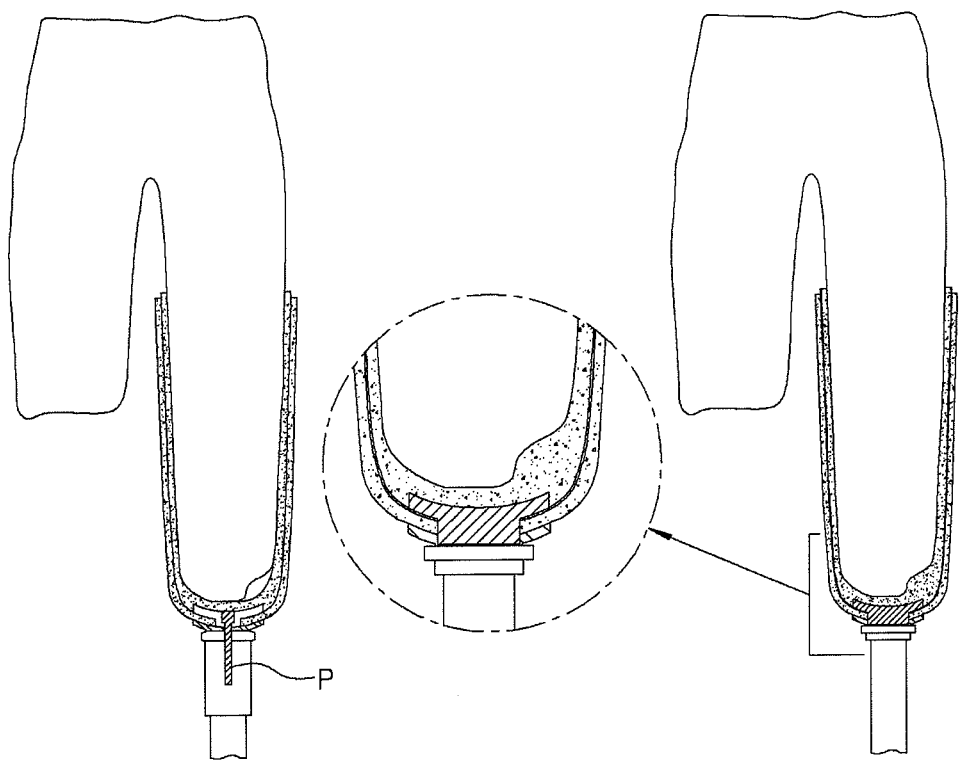
FIG. 2 is a configuration view showing the fastening of the magnetic locking device for an artificial limb according to the present invention (right) and the fastening of a pin locking device of the related art.

1: Magnetic lock case
2: Magnetic locking device
3: Battery
4: Current regulator
5: Power switch
6: Artificial limb connecting pyramid
7: Artificial limb connecting adaptor
8: Socket attachment member
9: Socket liner
10: Artificial limb
12: Core
13: Electric coil
14: Permanent magnet
20: Socket

BEST MODE

Hereinafter the present invention will now be described in more detail with reference to the accompanying drawings.

FIG. 1 is a cross-sectional view showing a structure for connecting an artificial limb 10 and a socket 20 using a magnetic locking device according to the present invention.

The artificial limb 10 includes a magnetic lock case 1, a magnetic locking device 2, a battery 3, a current regulator 4, a power switch 5, a limb connecting pyramid 6, and a limb connecting adaptor 7, and the socket 20 includes a socket liner 9 and a socket attachment member 8.

The magnetic lock case 1 is mounted on the distal end of the artificial limb 10, serves as a case to protect the magnetic locking device 2 by containing it therein, and is made of metal, plastic, or the like.

The magnetic locking device 2 is a magnet system that is constructed by combining permanent magnets and electromagnets, and is a device that connects the socket 20, which is worn on a stump, and the artificial limb 10 by using magnetic force.

The magnetic locking device 2 includes permanent magnets 14 for generating a magnetic field, a core 12 for transmitting the magnetic field generated by the permanent magnets 14 to the attachment member 8, and an electric coil 13 for facilitating electrical attachment and detachment in response to the magnetic field generated by the permanent magnets 14.

The battery 3 serves to power the magnetic locking device 2, and can be reused after recharging it when it is discharged, should it be made of a rechargeable secondary cell such as a lithium ion cell. The battery 3 can be used only when detaching the socket 20 in order to reduce power consumption. Although the battery 3 is shown as being positioned under the magnetic locking device 2, its position is not limited thereto but may be changed to other positions.

The current regulator 4 serves to induce a predetermined amount of current through the coil such that the battery 3 is fully charged, so that the battery 3 can also operate properly at the least amount of energy necessary to perform detachment. Although it is shown in the figure that the current regulator 4 is disposed under the magnetic locking device 2, its position is not limited thereto and may be changed to other positions.

The power switch 5 is a magnetic lock switch, and serves to switch on/off the supply of a current from the battery 3 to the coil of the magnetic locking device 2. The power switch 5 is typically used as an ON/OFF button. Although it is shown in the figure that the power switch 5 is disposed on the side of the magnetic locking device 2, its position is not limited thereto and may be changed to other positions.

The current regulator 4 and the power switch 5 are control devices that enable the socket 20 and the artificial limb 10 to be easily attached to and detached from each other. When detaching the socket 20, power is supplied to the magnetic locking device 2 by the power switch 5 to block the magnetic force of the permanent magnets, and the current of the battery 3 is controlled by the current regulator 4.

The artificial limb connecting pyramid 6 is a device that is disposed under the magnetic locking device 2 and serves to connect the magnetic locking device 2 to the body of the artificial limb 10. The artificial limb connecting pyramid 6 is made of aluminum, titanium, stainless steel, or the like.

The artificial limb connecting adaptor 7 is a device that is disposed under the artificial limb connecting pyramid 6, and serves to connect the magnetic locking device 2 to the body of the artificial limb 10.

The attachment member 8 is a part including a metal material that is attached to the lower end of the socket 20 such that it is attracted to the magnetic locking device 2.

The socket liner 9 is a liner disposed inside the socket 20. A socket 20 made of plastic is used in order to wear the artificial limb 10 on the stump, and a liner made of silicone is placed between the plastic socket 20 and the cut part in order to protect the skin and perform a buffer function. This silicone liner is referred to as the socket liner 9.

The socket liner 9 can have a dual structure that includes an upper inner portion into which the stump is received and a lower outer portion. The upper inner portion is made by shaping a low-hardness silicone material (Shore A hardness ranging from 5 to 20) in order to afford a smooth and cozy sensation when worn. The lower outer portion is made by shaping a high-hardness silicone material (Shore A hardness ranging from 30 to 60) in order to limit expansion and contraction due to the weight of the artificial limb 10 during walking.

In addition, a one-directional span raw material may be attached to the surface of the socket liner 9. When a user walks for a long time wearing the artificial limb 10, the silicone socket liner repeatedly expands and contracts, that is, it expands when the user swings it while walking due to its weight and contracts when the user places the foot on the ground. This, consequently, becomes a factor that causes abrasion owing to the repeated friction between the silicone socket liner and the skin on the stump. An abrasion refers to a wound in which the skin is damaged by an external force directed parallel to the skin, in particular, an external wound in which the skin is peeled off by being scraped or rubbed. In general, the outer skin is peeled off, lymph leaks, and bleeding occurs at the inner skin. The lymph and blood then solidify, thereby forming a scab. In order to prevent the abrasion through the friction on the stump, the one directional span raw material is attached to the surface of the socket liner 9. The one directional span raw material ensures that the socket liner 9 can expand and contract in the width direction but not in the longitudinal direction.

Figure 3:
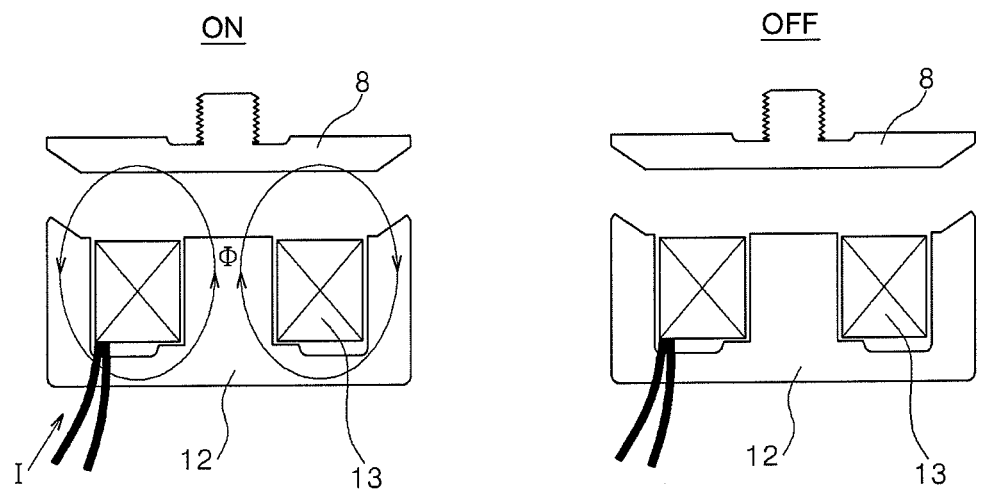
FIG. 3 is a schematic view showing the operating principle of an electromagnet type of structure.

FIG. 3 is a schematic view showing the operating principle of an electromagnet type of structure. As shown in FIG. 3, the electromagnet type of structure includes an electric coil 13 for generating a magnetic field and a core 12 for transmitting the magnetic field generated by the electric coil 13 toward the attachment member 8.

As shown in the left part of FIG. 3, when a current I is allowed to flow through the electric coil 13, a magnetic flux Φ occurs in the electric coil 13, and flows through the core 12 and the attachment member 8, thereby generating a force of attraction between the electromagnet and the attachment member 8. As shown in the right of FIG. 3, when a current is not allowed through the electric coil 13, no magnetic field is generated by the electric coil 13, and thus no force of attraction is generated between the electromagnet and the attachment member 8.

Although the electromagnet may be fabricated in any shape such as a rectangular or circular shape, the configuration that is intended in the present invention cannot be realized by the electromagnet itself. This is because a large capacity battery must be mounted since electric energy is required while the force of attraction is being generated. In addition, the volume and weight of the electromagnet disadvantageously increase, since a large size electric coil is required in order to decrease heat generated from the electromagnet.

Figure 4:
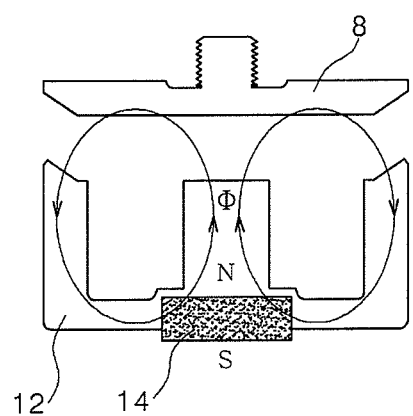
FIG. 4 is a schematic view showing the operating principle of a permanent magnet type of structure.

FIG. 4 is a schematic view showing the operating principle of a permanent magnet type of structure. As shown in FIG. 4, the permanent magnet type of structure includes a permanent magnet 14 for generating a magnetic field and a core 12 for transmitting the magnetic field generated by the permanent magnet 14 toward the attachment member 8. The permanent magnet 14 disposed inside the core 12 generates a magnetic flux Φ, which in turn flows through the core 12 and the attachment member 8, thereby generating a force of attraction between the permanent magnet 14 and the attachment member 8.

Since the permanent magnet type of structure does not have any means for blocking the magnetic field generated by the permanent magnet 14, the attachment member 8 must be forcibly detached using a physical force. Otherwise, it is required to adopt a structure in which another permanent magnet is disposed in order to redirect the magnetic flux Φ, which is directed toward the attachment member 8, into the core 12.

In these types of the permanent magnet structure, the circular permanent type of structure is simple, but a disabled person who has an impaired limb has difficulty detaching the artificial limb. If another permanent magnet is added in order to facilitate attachment and detachment, the volume and weight are disadvantageously increased.

Figure 5:
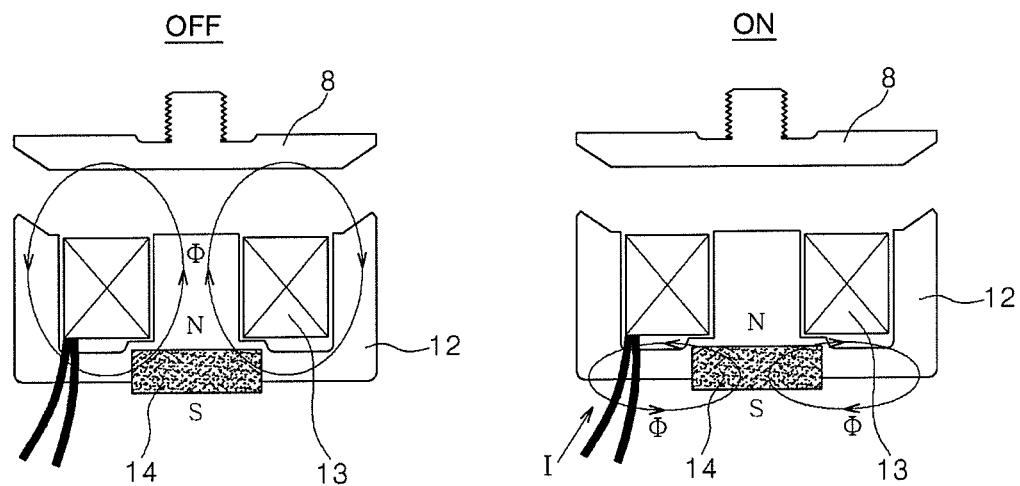
FIG. 5 is a schematic view showing the operating principle of an electro-permanent magnet type of structure.
Figure 6:
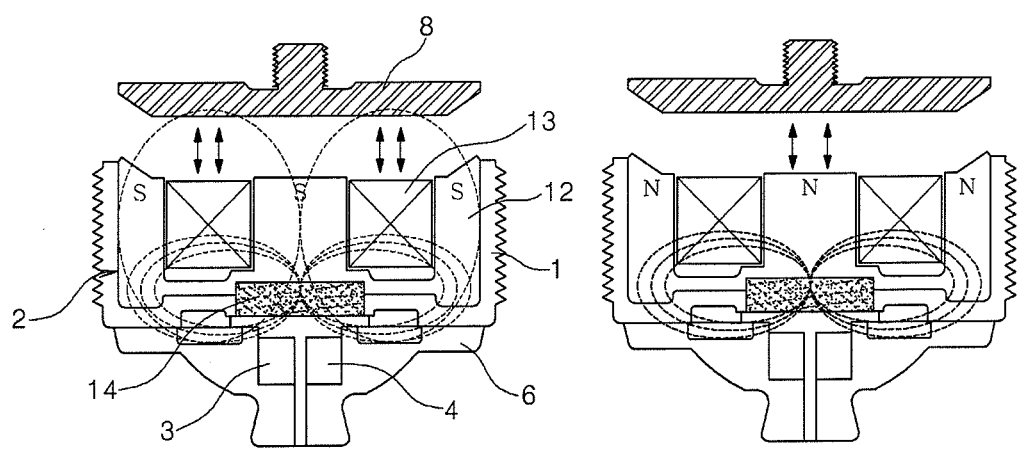
FIG. 6 is a cross-sectional view showing the operating principle of a magnetic lock according to the present invention (left: power off, right: power on)

FIG. 5 is a schematic view showing the operating principle of an electro-permanent magnet type of structure, and FIG. 6 is a cross-sectional view showing the operating principle of a magnetic lock according to the present invention (left: power off, right: power on).

As shown in FIG. 5 and FIG. 6, the electro-permanent magnet type of structure includes a permanent magnet 14 for generating a magnetic field, a core 12 for transmitting the magnetic field generated by the permanent magnet 14 toward the attachment member 8, and an electric coil 13 for electrically facilitating attachment and detachment in response to the magnetic field generated by the permanent magnet 14.

As shown in the left part of FIGS. 5 and 6, when the permanent magnet 14 is disposed inside the core 12, the permanent magnet 14 generates a magnetic flux Φ, which in turn flows through the core 12 and the attachment member 8, thereby generating a force of attraction between the permanent magnet 14 and the attachment member 8.

As shown in the right part of FIGS. 5 and 6, when a current I flows through the electric coil 13 to generate a magnetic field in the direction inverse to that of the magnetic field of the permanent magnet 14, the magnetic flux Φ generated by the permanent magnet 14 circulates inside the core 12, thereby canceling the force of attraction for the attachment member 8, so that the attachment member 8 can be easily detached.

The principle of the electro-permanent magnet type of structure is intended to redirect the magnetic field instead of removing the magnetic field generated by the permanent magnet. In particular, a circular electro-permanent magnet type of structure that can maintain constant performance without reducing the lifespan and the magnetic field of the permanent magnet is most suitable.

The necessities of the electro-permanent magnet locking device are as follows. Since a pin type connection is used for the artificial limb and the socket in the related art, a localized pressure may occur in the lower end of the stump around the pin. This becomes more serious if the stump is not round but a bone protrudes. In this case, repeated weight load may cause a cicatrix, inflammation, necrosis, or pain to the tissue of the stump. Such pain may cause abnormal gait and induce secondary diseases associated with the abnormal gait. Therefore, there is required a new connection structure that can reduce the localized pressure by uniformly distributing pressure across the lower end of the stump and uniformly apply weight load across the lower end of the stump.

The permanent magnet locking device has the following effects. The localized pressure concentration on the lower end of the stump, which appears in the pin type, can be prevented. As such, it is possible to prevent the cicatrix, inflammation, necrosis, or pain in the tissues of the stump by reducing the localized pressure. Since the pressure is uniformly distributed across the lower end of the stump, force is ideally distributed across the stump, and a balanced gait is enabled. Compared to the pin connection type of the related art, fatigue is reduced and an ideal gait similar to the normal gait is achieved.

Figure 7:
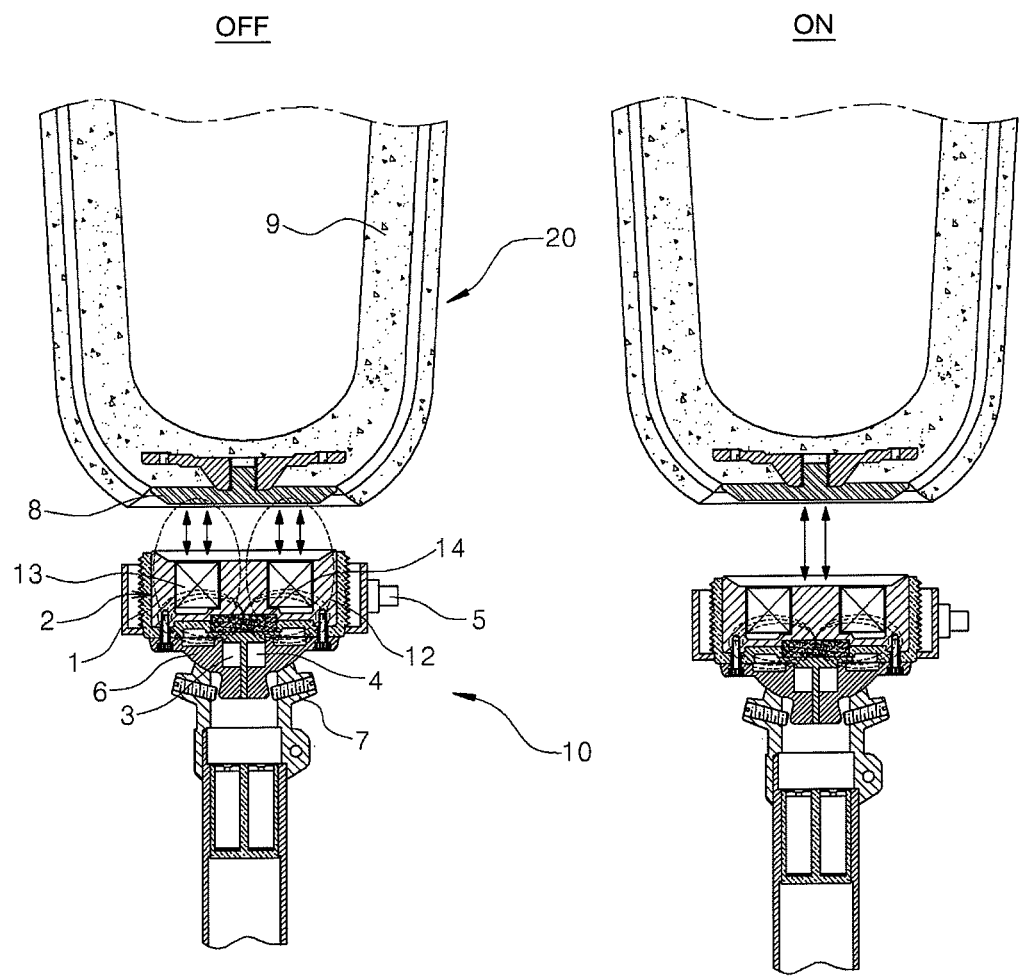
FIG. 7 is a configuration view showing the fastening of a magnetic locking device according to the present invention and a socket liner, which can be attached to and detached from the magnetic locking device using magnetic force.

FIG. 7 is a configuration view showing the fastening of a magnetic locking device and a socket liner according to the present invention, which can be attached to and detached from the magnetic locking device using magnetic force. As shown in FIG. 7, a metal attachment member 8, which can be attached to and detached from the magnetic locking device 2 in response to the magnetic force of the magnetic locking device 2, is attached to the lower end of the socket liner 9. The attachment member 8 can be fabricated in a circular global shape such that it can be attached to the magnetic locking device 2 with a greater attracting force. The attachment member 8 may include holes, which can be formed along the circumference of the attachment member 8 in order to increase the coupling force between the attachment member 8 and the socket liner 9. The holes can be bonded to the silicone material of the socket liner 9 such that the attachment member 8 can be efficiently coupled with the socket liner 9. The socket liner 9 can be molded into a shape so that some silicone part of the socket liner can be fixed to the holes. It is preferred that the attachment member 8 be made of an iron system material having a low alloy content such that the attachment member 8 can be easily attached to the magnet.

INDUSTRIAL APPLICABILITY

The electro-permanent magnet lock realized in the present invention uses both a permanent magnet and an electric coil in order to attract a metal object in the lower end of the socket using a force of the permanent magnet so that the object is not detached even if the magnet or a power system fails. By changing the polarity of the permanent magnet using a current supplied to the electric coil, it is possible to set the metal object to be attached or detached. Since electric power is supplied only for a short time during attachment and detachment, it is possible to save energy while ensuring safety and reliability. In addition, since electric power is supplied only when current is switched on/off, there is no temperature rise. This, consequently, prevents heat from being generated from the part on which the device is worn, thereby alleviating a stuffy sensation in the stump.

Furthermore, the magnetic lock using the electro-permanent magnet provides a large area for the connecting portion between the distal end of the stump and the artificial limb in order to ensure that walking is very stable and to prevent pain. If the distal end of the silicone socket liner is highly flexible, friction repetitively occurs between the skin of the stump and the silicone socket liner, thereby causing abrasion to the stump. However, the present invention can prevent the expansion and contraction of the socket liner during walking by providing a fixing mechanism based on surface contact instead of a fixing mechanism using a pin, thereby preventing abrasion.

The invention claimed is:

1. A structure for connecting an artificial limb and a socket, comprising:
   a magnetic locking device disposed on a distal end of the artificial limb, wherein the magnetic locking device comprises an electro-permanent magnet including a permanent magnet and an electromagnet,
   an attachment member disposed on a distal end of the socket, wherein the attachment member is attachable to and detachable from the magnetic locking device using magnetic force;
   a battery configured for powering the magnetic locking device;
   a current regulator configured for regulating a current supplied to the magnetic locking device; and
   a power switch configured for selectively allowing a supply of power to be provided from the battery to the magnetic locking device.

2. The structure of claim 1, wherein the magnetic locking device comprises:
   a core, wherein the permanent magnet is disposed inside the core and is configured to generate a first magnetic field and wherein the core is configured to transmit the first magnetic field toward the attachment member; and
   an electric coil disposed on the core, wherein the electric coil is configured to generate a second magnetic field that allows the attachment member to become easily attachable to and detachable from the magnetic locking device.

3. The structure of claim 2, wherein a magnetic flux generated by the permanent magnet flows through the core and the attachment member to generate a force of attraction between the permanent magnet and the attachment member, and a current is induced through the electric coil such that the second magnetic field is generated in a direction inverse to that of the first magnetic field of the permanent magnet in order to block magnetic force generated by the permanent magnet, so that the magnetic flux generated by the permanent magnet circulates inside the core, thereby canceling the force of attraction between the permanent magnet and the attachment member, whereby the permanent magnet and the attachment member become easily detachable from each other.

4. The structure of claim 1, wherein the supply of power from the battery is used only when detaching the artificial limb and the socket from each other.

5. The structure of claim 1 further comprising:
   a socket liner made of silicone disposed inside the socket.

6. The structure of claim 5, wherein the socket liner has a dual structure including an inner member, which is made of silicone having a Shore A hardness ranging from 5 to 20, and an outer member, which is made of silicone having a Shore A 10 hardness ranging from 30 to 60.

* * * * *